(12) United States Patent
Rentas Torres

(10) Patent No.: US 7,241,180 B1
(45) Date of Patent: Jul. 10, 2007

(54) MEDICAL ELECTRICAL LEAD CONNECTOR ASSEMBLY

(75) Inventor: Douglas Rentas Torres, Villalba, PR (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/343,859

(22) Filed: Jan. 31, 2006

(51) Int. Cl.
*H01R 13/648* (2006.01)

(52) U.S. Cl. .................. 439/668; 439/669; 439/909

(58) Field of Classification Search ............... 439/668, 439/669, 909; 607/37
See application file for complete search history.

(56) References Cited

U.S. PATENT DOCUMENTS

| | | | |
|---|---|---|---|
| 4,951,687 A | 8/1990 | Ufford et al. | |
| 5,070,605 A | 12/1991 | Daglow et al. | |
| 5,304,219 A * | 4/1994 | Chernoff et al. | 607/122 |
| 6,786,774 B2 * | 9/2004 | Haas et al. | 439/669 |
| 6,817,905 B2 | 11/2004 | Zart et al. | |
| 6,847,845 B2 | 1/2005 | Belden | |
| 6,854,994 B2 | 2/2005 | Stein et al. | |
| 6,895,276 B2 | 5/2005 | Kast et al. | |
| 6,912,423 B2 | 6/2005 | Ley et al. | |
| 6,913,478 B2 * | 7/2005 | Lamirey | 439/259 |
| 7,108,549 B2 * | 9/2006 | Lyu et al. | 439/587 |
| 7,175,478 B2 * | 2/2007 | Olivier | 439/669 |
| 2005/0043771 A1 * | 2/2005 | Sommer et al. | 607/37 |
| 2005/0171509 A1 | 8/2005 | Hector | |
| 2005/0221671 A1 | 10/2005 | Lyu et al. | |

\* cited by examiner

*Primary Examiner*—Tho D. Ta
(74) *Attorney, Agent, or Firm*—Carol F. Barry; Girma Wolde-Michael

(57) ABSTRACT

A connector for a medical electrical lead includes a single connector, which delivers three or more conductors to an implantable medical device (IMD). The connector includes integrated multiple electrode rings and conductors, and has a modular system of connector and spacer blocks for routing the conductors to a lead body.

35 Claims, 9 Drawing Sheets

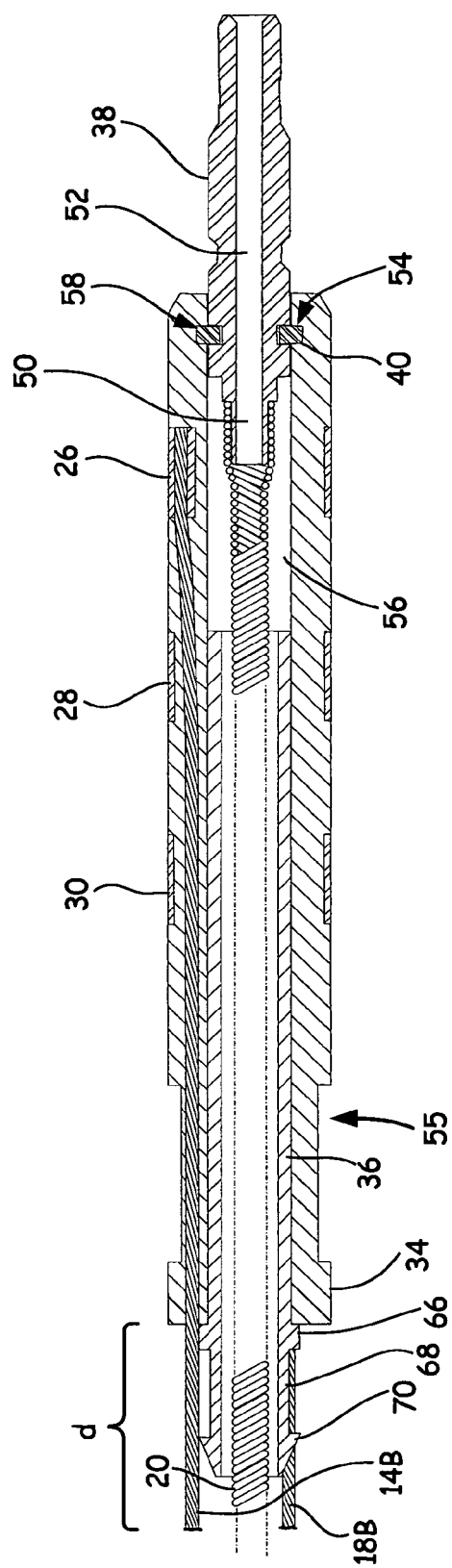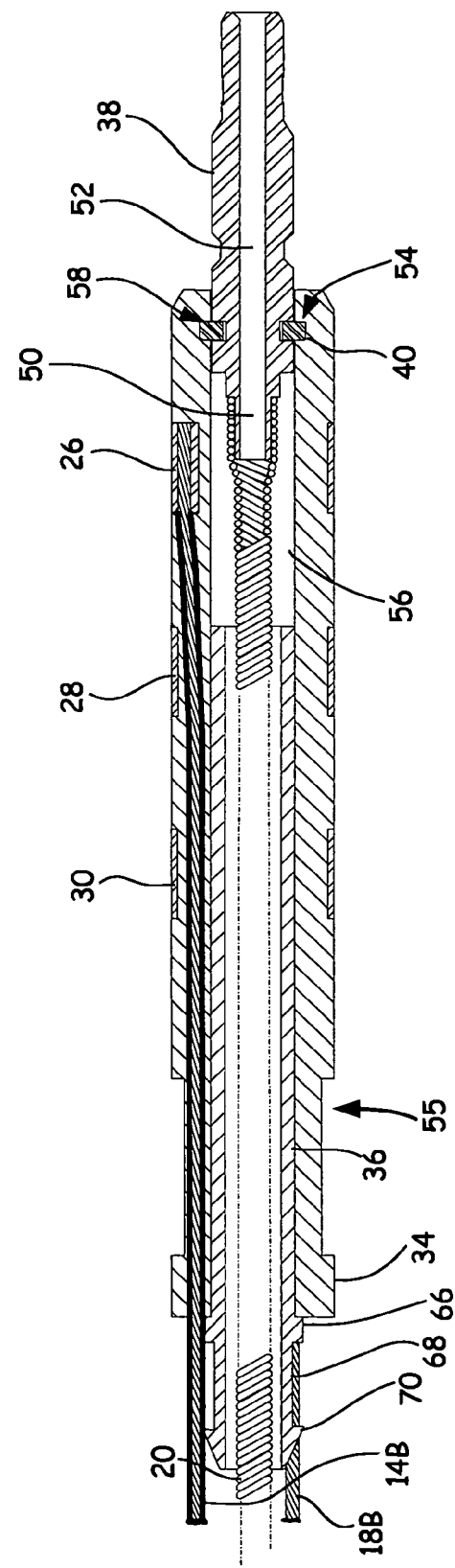

MEDICAL ELECTRICAL LEAD CONNECTOR ASSEMBLY

BACKGROUND OF THE INVENTION

The present invention relates generally to implantable medical device (IMD) leads for delivering active electrodes to various places in a human body, such as the heart. In particular, the present invention relates to connectors for connecting a lead with an IMD.

Advances in technology have led to IMDs having increased capabilities for performing therapeutic, diagnostic and other functions. Such advances can require the use of leads carrying additional electrodes, which require additional conductors that run from the IMD to a distal end of the lead. Recently, high voltage (HV), quadripolar leads having four conductors have been introduced for tachyarrythmia management and other applications. These leads include an industry standard IS-1 connector pin for connecting the IMD with a typical coil conductor and a sensing electrode conductor for performing Brady-type pacing. In addition, for performing other pacing, sensing, defibrillation therapy and diagnostic functions, for example, in the superior vena cava (SVC) or right ventricle (RV), additional conductors are connected to the IMD with standard DF-1 connector pins. Thus, these leads require up to three connector pins for inserting into the IMD. Because an additional connector port is necessary for each connector pin, the increased number of pins can result in an increased size of the IMD, which requires a larger space-volume and may pose hermiticity and patient comfort issues. Therefore, there is a need for a lead connector capable of connecting multiple conductors with a single connector pin.

BRIEF SUMMARY OF THE INVENTION

The present invention is directed to a connector for a medical electrical lead in which a single connector delivers three or more conductors to an implantable medical device (IMD). The invention includes a connector having multiple integrated electrode rings and conductors, and having a modular system of connector and spacer blocks for routing the conductors to a lead body.

BRIEF DESCRIPTION OF THE DRAWINGS

FIG. 3A shows a cross sectional view of a connector assembly having single layer polytetrafuoroethylene (PTFE) insulated wire conductors.

FIG. 3B shows a cross sectional view of a connector assembly having double layer PTFE insulated wire conductors.

DETAILED DESCRIPTION

Figure 1A:
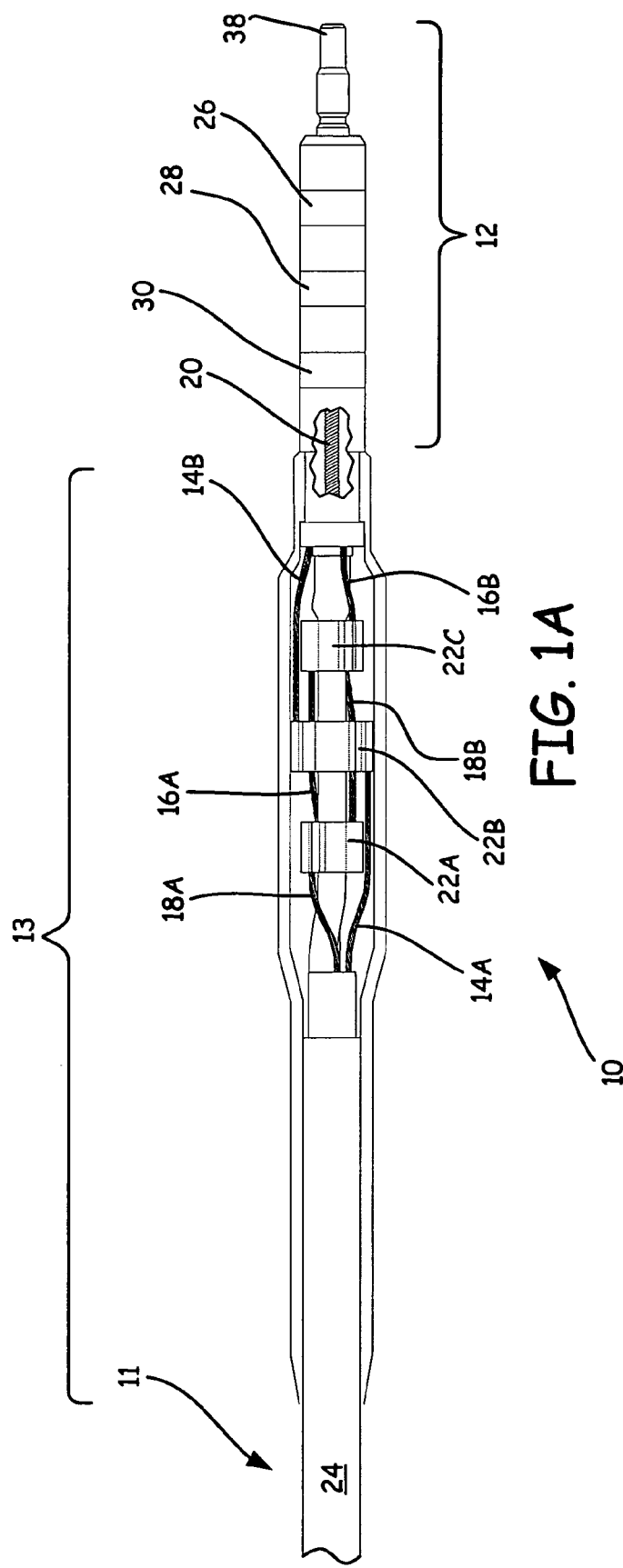
FIGS. 1A and 1B show partially cut-away views of a lead connector of the present invention.
Figure 1B:
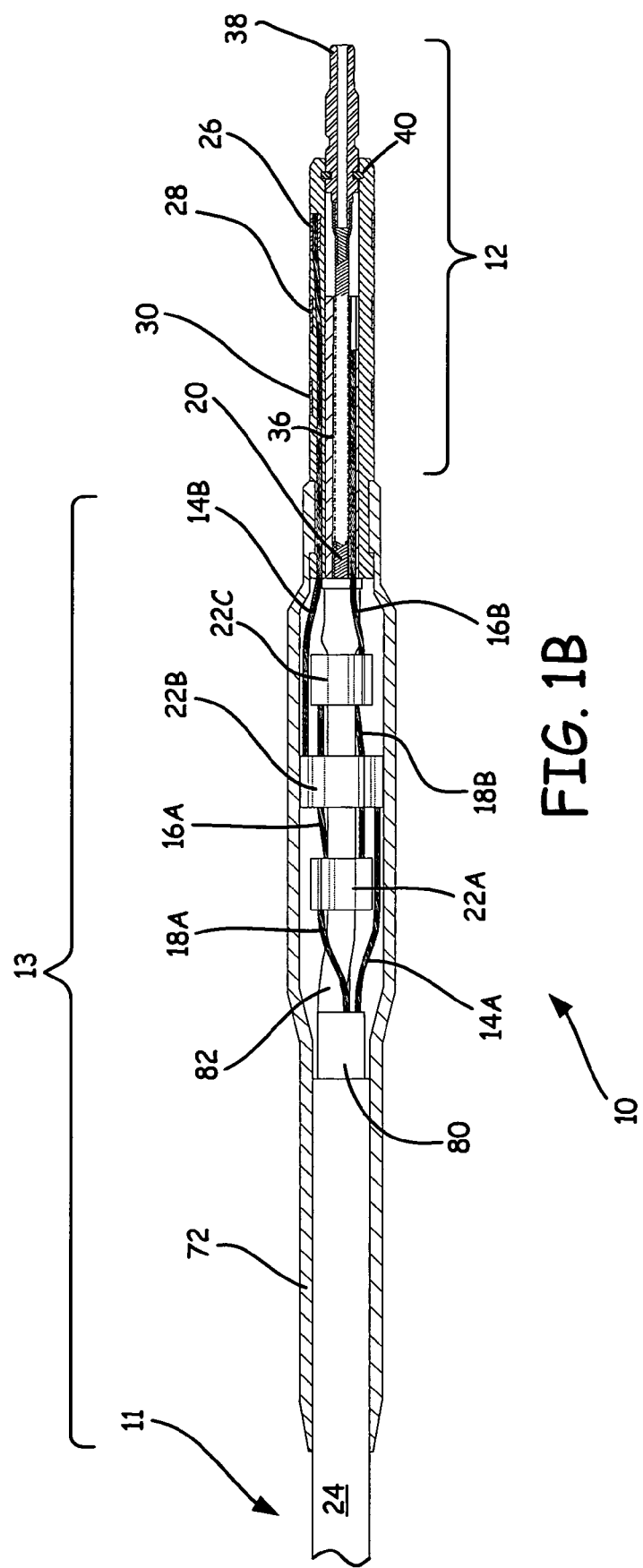

FIGS. 1A and 1B show a partially cut-away views of lead connector 10, which is used to connect multi-conductor lead 11 with an implantable medical device (IMD), such as a cardiac pacing pulse generator or implantable cardioverter defibrillator, through a single connector. Lead connector 10 is positioned at a proximal end of lead 11, and is comprised of connector assembly 12 and transition assembly 13. In the embodiment shown, lead 11 comprises a quadripolar construction in which three wire conductors (conductors 14A, 16A, and 18A) and one coil conductor (conductor 20) are delivered to or near the distal end of lead 11. Transition assembly 13 includes connector blocks 22A, 22B and 22C, which are used to coordinate the interconnection of the conductors from lead 11 to connector assembly 12.

In the embodiment described, three wire conductors are used, however it is contemplated that the lead connector of the present invention can be adapted for leads having two, four or more wire conductors. Lead 11 also includes sheathing 24, which comprises a flexible, protective barrier between the conductors and the body in which lead 11 is implanted. Sheathing 24 can be formed of silicone, polyurethane, or a non-porous or dense PTFE.

Lead connector 10 delivers each of the conductors to a single uni-axial connector body, such that a single connector links all four conductors with the IMD. Transition assembly 13 is used to deliver conductors 14A, 16A, 18A and 20 to connector assembly 12, which can be fitted with a connector socket of an IMD. Connector assembly 12 comprises a universal connection to a variety of IMDs in which up to four conductors can be linked with the IMD. Connector assembly 12 is a modular assembly that can be separately manufactured, assembled and distributed for use with a variety of leads. Likewise, transition assembly 13 is a modular, adaptable system that can be configured for linking various leads having up to four conductors to connector assembly 12.

Transition assembly 13 connects wire conductors 14A, 16A and 18A of lead 11 with conductors 14B, 16B and 18B of connector assembly 12, while also allowing coil conductor 20 to travel uninterrupted from the proximal end to the distal end of lead 11. Connector block 22B connects wire conductor 14A with wire conductor 14B and electrode ring 26, thus forming a circuit with an electrode positioned at the distal end of lead 11 for performing sensing functions within a heart. Connector block 22C connects conductor 16A with wire conductor 16B and electrode ring 28, thus forming a circuit with, for example, a right ventricle defibrillation coil electrode (RV defib coil). Connector block 22A connects wire conductor 18A with wire conductor 18B and electrode ring 30, thus forming a circuit with, for example, a superior vena cava defibrillation coil electrode (SVC defib coil). Coil conductor 20, which runs concurrently through lead connector assembly 10, is connected with connector pin 38 and is used in conjunction with electrode ring 26 and wire conductors 14A and 14B in performing heart pacing functions.

Figure 2:
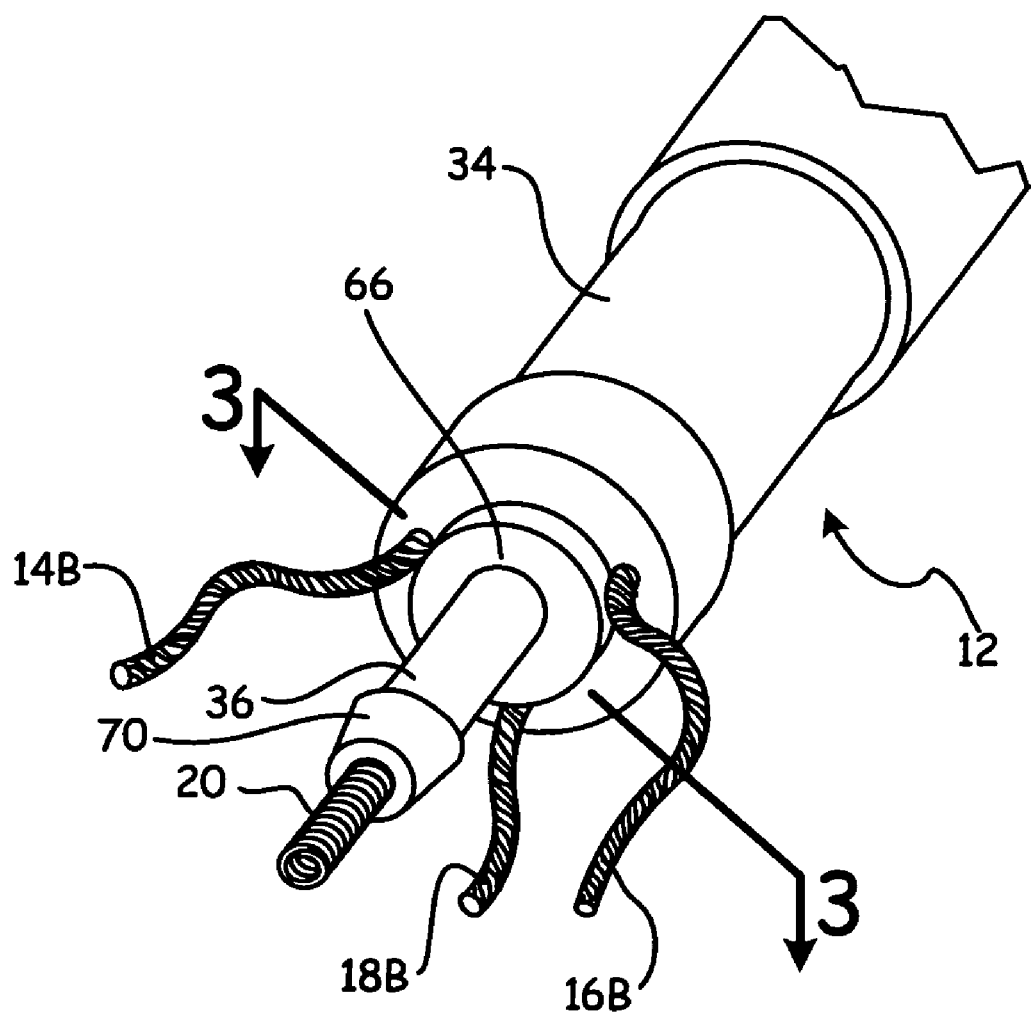
FIG. 2 shows the distal end of a connector body having three wire conductors.

FIG. 2 illustrates the distal end of connector assembly 12, showing the distal end of wire conductors 14B, 16B and 18B. Connector assembly 12 includes connector body 34 and retainer 36. Wire conductors 14B, 16B and 18B are spaced one hundred twenty degrees apart around the circumference of connector body 34. Conductors 14B, 16B and 18B are integrally formed with connector body 34, such as in a molding process. Wire conductors 14B, 16B and 18B can be selectively cut off of connector body 34 when being connected with leads having fewer than three wire conductors. Retainer 36 is inserted into connector body 34 and is used to join connector assembly 12 with transition assembly 13.

FIG. 3A shows a cross section of connector assembly 12 of lead body connector 10 taken along section 3—3 of FIG. 2. FIG. 3A shows lead connector assembly 12 having a single coating of PTFE insulation on wire conductors 14B, 16B and 18B. FIG. 3B shows another embodiment of connector assembly 12 in which wire conductors 14B, 16B and 18B include a double coating of PTFE insulation. The embodiments of lead body 10 shown in FIG. 3A and FIG. 3B are similarly constructed and include like element numbers. FIGS. 3A and 3B will be discussed concurrently.

Connector assembly 12 is comprised of electrode rings 26, 28 and 30, connector body 34, retainer 36, connector pin 38, locking mechanism 40 and wire conductors 14B, 16B and 18B (of which only wire conductor 14B and 18B can be seen in FIGS. 3A and 3B). Connector body 34 and retainer 36 are typically comprised of a urethane material. Wire conductors 14B, 16B and 18B are typically comprised of silver core wires, but can be of any suitable construction and material.

Figure 4:
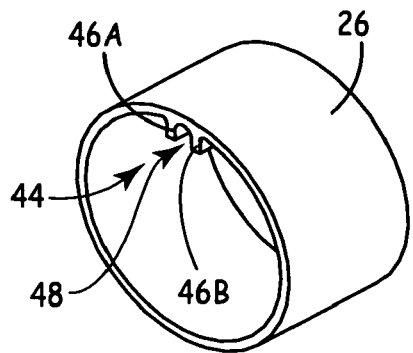
FIG. 4 shows an electrode ring having a wisdom tooth connector.

Wire conductors 14B, 16B and 18B are pre-assembled with electrode rings 26, 28 and 30, respectively. FIG. 4 shows electrode ring 26, which is also representative of electrode rings 28 and 30. Electrode ring 26 is comprised of a conducting, non-reactive material, such as titanium, and typically includes a conductive, corrosion resistant coating. Electrode ring 26 includes wisdom tooth connecting mechanism 44, which is comprised of spaced rails 46A and 46B that form channel 48. One of the wire conductors (e.g. wire conductor 14B) is laid flat into channel 48. Any insulation around the wire conductor along the segment that interacts with electrode ring 26 is removed such that a conductive link is formed, as shown, for example, in FIG. 3B. Rails 46A and 46B are then crimped inward around the wire conductor, thus forming a mechanical bond having tensile strength suitable for withstanding tension imposed on lead connector assembly 10 during installation and operation of lead 11. The crimping of rails 46A and 46B also improves the electrical connection between the wire conductor and electrode ring 26.

Returning to FIG. 3A, the wire conductor and electrode ring assemblies are then integrally formed with connector body 34, such as with a molding process. Wire conductors 14B, 16B and 18B extend a length d beyond the distal face of connector body 34 in order that they can be joined with transition assembly 13. Typically, length d is about three to four inches. Depending on the type of lead with which connector assembly 12 is intended to be used, the wire conductors can be selectively trimmed from connector body 34. For example, if connector assembly 12 is to be used with a lead having only one wire conductor in addition to a coil conductor, two of wire conductors 14B, 16B and 18B can be cut off at the distal face of connector body 34. Alternatively, wire conductors 14B, 16B and 18B of connector assembly 12 can be joined with other types of transition assemblies or directly with lead 11. Electrode rings 26, 28 and 30 and wire conductors 14B, 16B and 18B are therefore assembled to form connector body 34, which is manufactured as a separate part that can be customized for use in different applications.

Once electrode rings 26, 28 and 30 and wire conductors 14B, 16B and 18B are assembled to form connector body 34, connector pin 38 is assembled with coil conductor 20. Connector pin 38, which is comprised of a conducting material, such as titanium, includes post 50, lumen 52 and circumferential groove 54. Post 50 is inserted into coil conductor 20, and bonded with a welding or soldering procedure. Lumen 52 accepts a stylet used to guide lead 11 into a body during implanting of an IMD. Connector pin 38 also includes circumferential groove 54, which is used in conjunction with locking mechanism 40 to retain connector pin 38 with respect to connector body 34.

After coil conductor 20 has been assembled with connector pin 38, connector pin 38 is assembled with connector body 34. Connector body 34 includes sheathing groove 55, central channel 56 and locking channel 58. Sheathing groove 55 is used to secure a protective sheathing around transition assembly 13. Connector pin 38 is inserted into central channel 56 of connector body 34, along with coil conductor 20, until circumferential groove 54 aligns with locking channel 58. Once they are aligned, locking mechanism 40 can be assembled with connector body 34.

Figure 5:
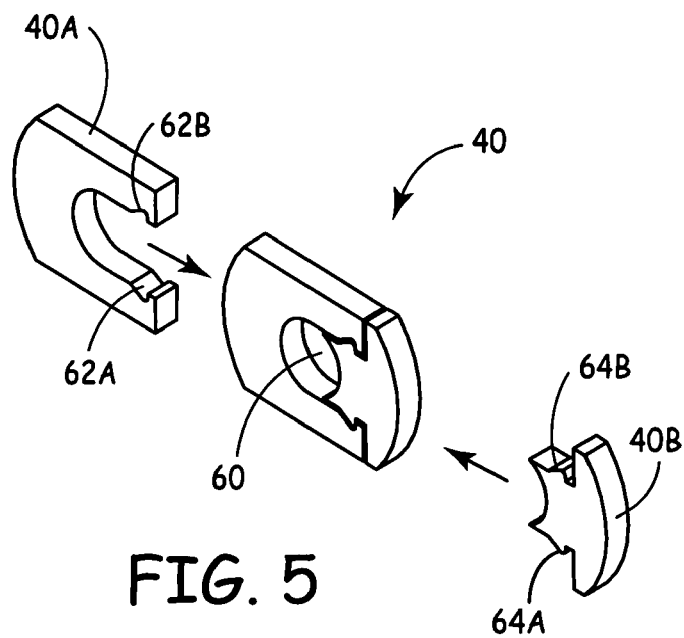
FIG. 5 shows a locking mechanism for a connector assembly.

As shown in FIG. 5, locking mechanism 40 includes two interlocking pieces: collar 40A and key 40B. Collar 40A prevents connector pin 38 from disengaging from connector body 34. Key 40B prevents collar 40A from disengaging connector pin 38. Collar 40A is inserted into locking channel 58 and circumferential groove 54 from one side of connector assembly 13, while key 40B is inserted through the opposite side. The outer extent of collar 40A and key 40B mates with locking channel 58 and the inner extent of collar 40A and key 40B mates with circumferential groove 54. Movement of connector pin 38 along the axis of connector body 34 is thereby prevented. Collar 40A includes notches 62A and 62B, which receive teeth 64A and 64B of key 40B. Teeth 64A and 64B allow key 40B to be inserted into notches 62A and 62B of collar 40A, but prevent key 40B from disengaging from collar 40A. Once assembled, collar 40A and key 40B form a circular yoke 60, which allows connector pin 38 to rotate in central channel 56.

To complete the assembly of connector assembly 12, retainer 36 is placed around coil conductor 20 and inserted into central channel 56 until flange 66 engages the distal face of connector body 34. Alternatively, retainer 36 could also be placed around coil conductor 20 before connector pin 38 is linked with connector body 34. Retainer 36 provides an additional insulating layer between coil conductor 20 and electrode rings 26, 28 and 30. The diameter of retainer 36 is slightly smaller than the diameter of central channel 56 such that a press fit connection is formed. There are several advantages of a press fit type connection. Previously, urethane connector pieces have been joined together with adhesives that require time to dry and sometimes caused deformation of the urethane pieces due to melting. Thus, press-fitting retainer 36 into connector body 34 avoids the necessity of special equipment and knowledge typically required in adhesive bonding. The press fit connection also prevents fluid from seeping into connector body 34. Retainer 36 includes connector post 68, which includes flange 70, for linking connector assembly 12 with transition assembly 13.

Figure 6:
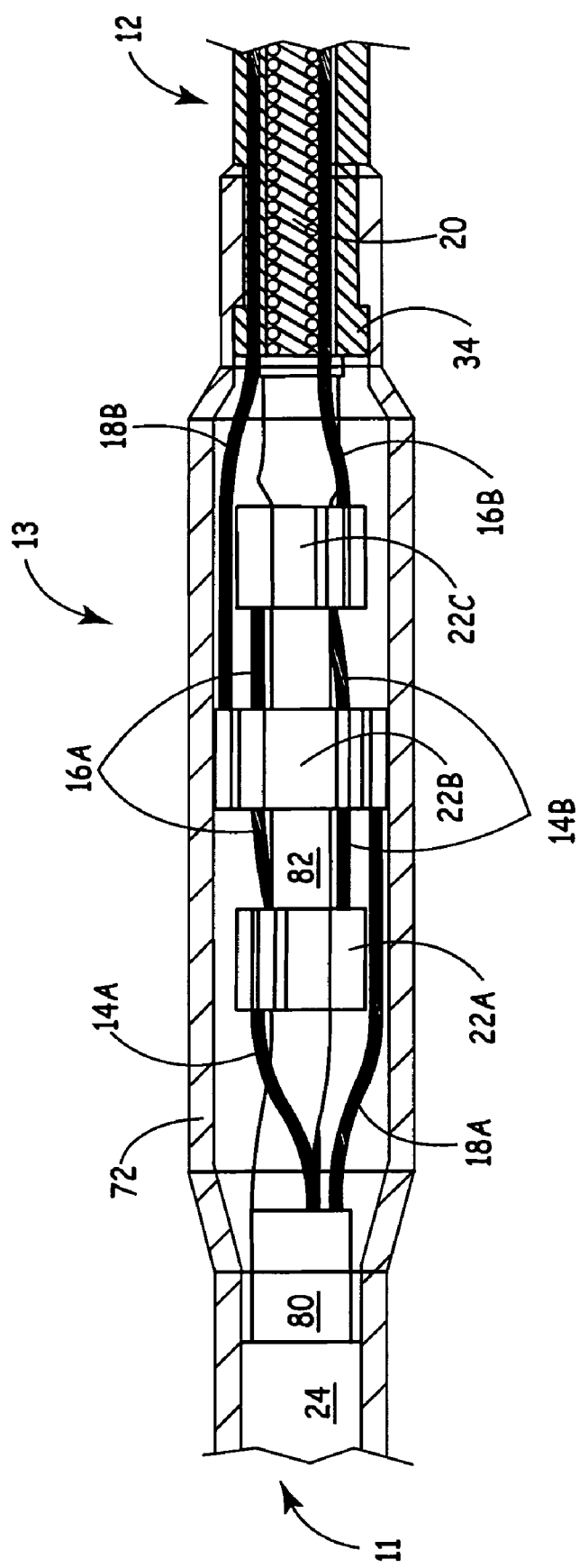
FIG. 6 shows a transition assembly of the lead connector of the present invention.

FIG. 6 shows a partial cross sectional view of transition assembly 13 connected with connector assembly 12. Transition assembly 13 joins connector assembly 12 with lead 11, and orchestrates the connection and arrangement of the conductors or each component. Transition assembly 13 includes first connector block 22A, second connector block 22B, third connector block 22C and sheathing 72. Lead 11 includes sheathing 24, multilumen tube 80, coil sheathing 82, and wire conductors 14A, 16A and 18A. Sheathing 72 and connector assembly 12 are shown in cross section, while the interior of transition assembly 13 is shown in full to show the inter-linking of the wire conductors.

Transition assembly 13 is first linked with connector assembly 12 with coil conductor 20 and coil sheathing 82. Coil conductor 20 is inserted into sheathing 82 up to the distal face of connector body 34. Sheathing 82 fits around post 50 of retainer 36 and is retained by tension in sheathing 82. This connection also avoids the necessity of adhesive bonding, which has the same benefits as described above. Coil sheathing 82 runs the length of transition assembly 13.

Figure 7:
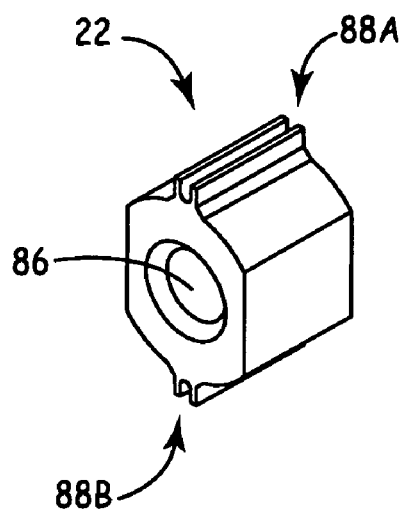
FIG. 7 shows a connector block having wisdom tooth connectors.

FIG. 7 shows connector block 22, which is representative of connector blocks 22A–22C. Connector block 22 includes center bore 86, first wisdom tooth connector 88A and second wisdom tooth connector 88B. Connectors 88A and 88B link wire conductors 14A, 16A and 18A of lead 11 with wire conductors 14B, 16B and 18B of connector assembly 12, respectively. Connectors 88A and 88B are similar in construction to wisdom tooth connector 44 of electrode ring 42, in that they are comprised of opposing rails to form a channel in which a conductor is laid. The opposing rails are then crimped to form a mechanical bond having adequate tensile strength. The crimp also improves the electrical contact between connector block 22 and the conductor. Wisdom tooth connectors 88A and 88B are placed one hundred eighty degrees apart on the outer periphery of connector block 22; one at the top and one at the bottom. Connector block 22 can be used, however, in any orientation.

Connector block 22 is comprised of a conductive body having a diameter approximating the diameter of connector body 34. The sides of connector block 22 are trimmed down to allow other conductors, not attached to connector block 22, to travel past connector block 22 within transition assembly 13. Typically, connector block 22 is comprised of titanium, but any acceptable conductive, non-reactive metal can be used.

Returning to FIG. 6, wire conductors 14B, 16B and 18B extend from the distal face of connector body 34 and conductors 14A, 16A and 18A extend from the proximal end of lead 11. The wire conductors are joined with connector blocks 22A, 22B and 22C. Connector blocks 22A, 22B and 22C are spaced equally apart on coil sheathing 82 and orientated along its axis one hundred twenty degrees apart, such that each wisdom tooth connector has clear access to the proximal end of lead 11 and the distal face of connector body 34. In other words, wisdom tooth connectors are positioned at 12, 2, 4, 6, 8 and 10 o'clock with respect to the distal face of connector body 34. Any insulating layers surrounding conductors 14A, 16A, 18A, 14B, 16B and 18B are removed where the conductors are to be joined with the wisdom tooth connectors so that conductive connections can be made.

Connector block 22B is positioned near the center of transition assembly 13, with its wisdom tooth connectors positioned at 12 and 6 o'clock. Wire conductor 18B extends from the top of connector body 34 to the wisdom tooth connector of connector block 22B at 12 o'clock. Wire conductor 18B is positioned within the channel of the wisdom tooth connector and the rails are crimped around conductor 18B to form an electrically conductive connection. Any excess length of conductor 18B, beyond what is necessary to completely join with connector block 22B, is cut away. Similarly, wire conductor 18A extends from near the bottom of lead 11 to the wisdom tooth connector of connector block 22B at 6 o'clock. Wire conductor 18A is positioned within the channel of the wisdom tooth connector and the rails are crimped around conductor 18A to form an electrically conductive connection. Any excess length of conductor 18A, beyond what is necessary to completely join with connector block 22B, is cut away. Thus, wire conductor 18A is conductively linked with wire conductor 18B.

Connector block 22C is positioned near the proximal end of transition assembly 13, with its wisdom tooth connectors positioned at 4 and 10 o'clock. Wire conductor 16B extends from the 4 o'clock position of connector body 34 to the wisdom tooth connector of connector block 22C at 4 o'clock. Wire conductor 16B is positioned within the channel of the wisdom tooth connector and the rails are crimped around conductor 16B to form an electrically conductive connection. Any excess length of conductor 16B, beyond what is necessary to completely join with connector block 22C, is cut away. Similarly, wire conductor 16A extends from near the bottom of lead 11 and runs past connector blocks 22A and 22B to the wisdom tooth connector of connector block 22C at 10 o'clock. Wire conductor 16A is positioned within the channel of the wisdom tooth connector and the rails are crimped around conductor 16A to form an electrically conductive connection. Any excess length of conductor 16A, beyond what is necessary to completely join with connector block 22C, is cut away. Thus, wire conductor 16A is conductively linked with wire conductor 16B.

Connector block 22A is positioned near the distal end of transition assembly 13, with its wisdom tooth connectors positioned at 2 and 8 o'clock. Wire conductor 14B extends from the 8 o'clock position of connector body 34 to the wisdom tooth connector of connector block 22A at 8 o'clock. Wire conductor 14B is positioned within the channel of the wisdom tooth connector and the rails are crimped around conductor 14B to form an electrically conductive connection. Any excess length of conductor 14B, beyond what is necessary to completely join with connector block 22A, is cut away. Similarly, wire conductor 14A extends from near the bottom of lead 11 to the wisdom tooth connector of connector block 22A at 2 o'clock. Wire conductor 14A is positioned within the channel of the wisdom tooth connector and the rails are crimped around conductor 14A to form an electrically conductive connection. Any excess length of conductor 14A, beyond what is necessary to completely join with connector block 22A, is cut away. Thus, wire conductor 14A is conductively linked with wire conductor 14B.

Once all the conductors have been joined with connector blocks 22A, 22B and 22C, transition assembly sheathing 72 is positioned around transition assembly 13. The distal end of sheathing 72 is fitted around sheathing 24 at the proximal end of lead 11. The proximal end of sheathing 72 is connected with the distal end of connector body 34, and is fitted around sheathing groove 55.

Transition assembly 13 achieves the electrical connection of the wire conductors of lead 11 with the wire conductors of connector assembly 12, while maintaining electrical isolation of each conductor circuit. In the embodiment shown in FIG. 6, the wire conductors are covered by a single layer of polytetrafluoroethylene (PTFE) insulation. It is advantageous to include insulation on each wire conductor in order to avoid electrical interference with the signal carried by each conductor within transition assembly 13. In another, such as shown in FIG. 3B, a second PTFE coating is added to the conductors to ensure that the signal carried by each conductor does not produce noise or interference in nearby conductors, especially in transition assembly 13. The insulating layers can be added to the conductors during manufacture, such as during extruding of the wires.

Transition assembly 13 also provides a flexible junction that maintains strong tensile strength due to the crimping mechanism of the wisdom tooth connectors. Although the connector blocks are discussed as being set at positions relative to the distal face of connector body 34, this is only intended to describe their approximate position. Once the connector blocks are assembled, they are free to rotate around coil sheathing 82, which also aids in tension dissipation in the conductors and flexibility of transition section 13.

Figure 8:
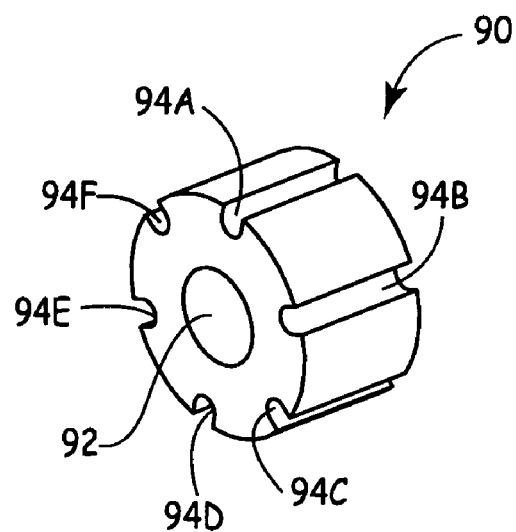
FIG. 8 shows a spacer block for use in a transition assembly.
Figure 9:
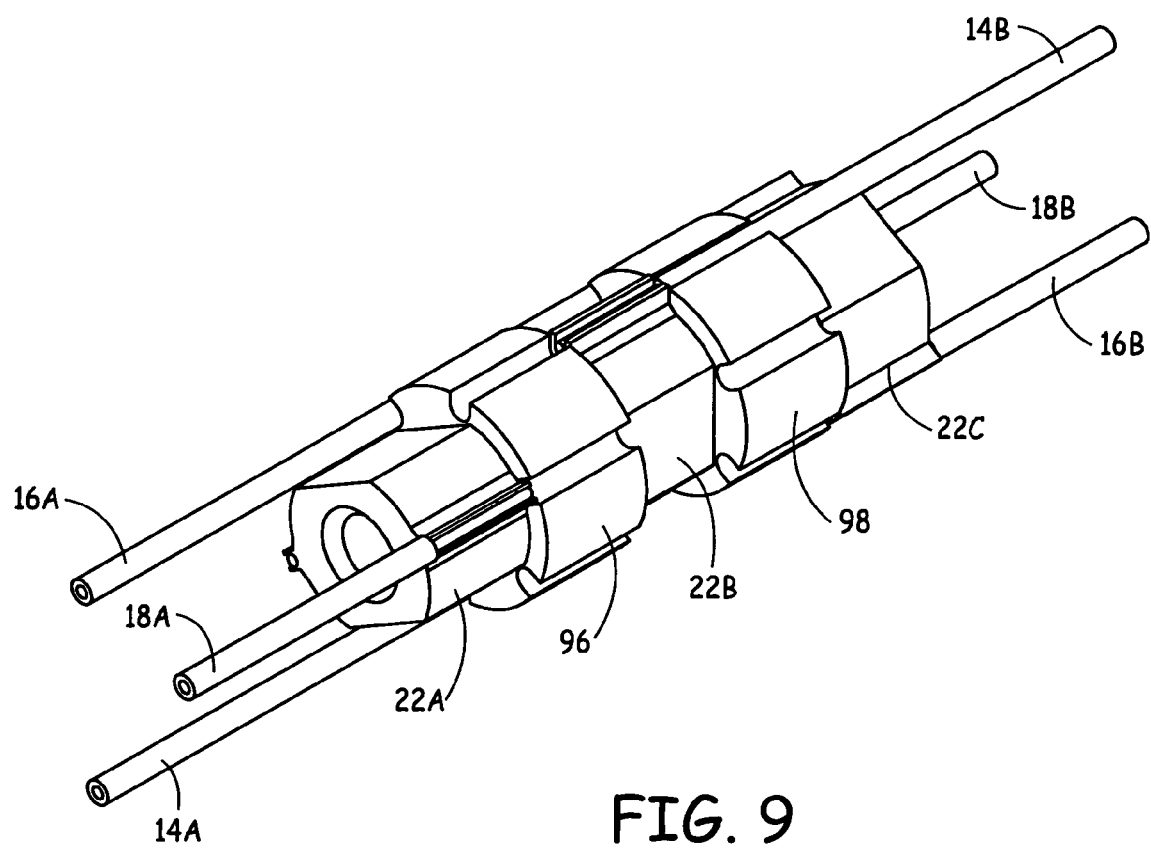
FIG. 9 shows a transition assembly comprised of connector blocks and spacer blocks.

In another embodiment of the invention, illustrated in FIGS. 8 and 9, transition assembly 13 is fitted with spacer blocks to dissipate some of the tension produced in the conductors during handling of lead 11. FIG. 8 shows spacer block 90, which comprises a circular disk having central bore 92 and peripheral channels 94A–94F. Central bore 92 allows spacer block 90 to be fitted around coil sheathing 82, in between connector blocks 22A–22C. Peripheral channels 94A–94F allow wire conductors travelling between connector blocks 22A–22C to be laid across spacer block 90. Peripheral channels 94A–94F have diameters large enough to accept insulated wire conductors. Peripheral channels 94A–94F are spaced around the circumference of spacer block 90 sixty degrees apart (i.e. at 12, 2, 4, 6, 8 and 10 o'clock with respect to the distal face of connector body 34). Spacer block 90 provides tension relief of the wire conductors by preventing wire conductors 14A, 16A, 18A, 14B, 16B and 18B from bending or kinking. Spacer block 90 is preferably composed of silicone rubber, but can be made of any suitable insulating and dampening material.

FIG. 9 shows an embodiment of transition assembly 13 provided with spacer blocks 96 and 98. Conductors 14A, 16A, 18A, 14B, 16B and 18B are shown as connected with connector blocks 22A–22C in FIG. 9. Connector blocks 22A, 22B and 22C are co-axially aligned on coil sheathing 82 of coil conductor 20, which has been omitted for clarity. Spacer block 96 is disposed on coil sheathing 82 between connector blocks 22A and 22B, and spacer block 98 is disposed on coil sheathing 82 between connector blocks 22B and 22C.

Wire conductor 14B extends distally in the 12 o'clock position, past connector block 22C and through a channel in spacer block 98 in the 12 o'clock position and into a wisdom tooth connecting mechanism of connector block 22B. Wire conductor 14A extends proximally in the 6 o'clock position, past connector block 22A and through a channel in spacer block 96 in the 6 o'clock position and into a wisdom tooth connecting mechanism of connector block 22B. Thereby, conductors 14B and 14A are conductively joined at connector block 22B.

Wire conductor 16B extends distally in the 4 o'clock position and into a wisdom tooth connecting mechanism of connector block 22C. Wire conductor 16A extends proximally in the 10 o'clock position past connector block 22A, through a channel in spacer block 96 in the 10 o'clock position, past connector block 22B, through a channel in spacer block 98 in the 10 o'clock position and into a wisdom tooth connecting mechanism of connector block 22C in the 10 o'clock position. Thereby, conductors 16B and 16A are conductively joined at connector block 22C.

Wire conductor 18B extends distally in the 8 o'clock position, past connector block 22C, through a channel in spacer block 98 in the 8 o'clock position, past connector block 22B, through a channel in spacer block 96 in the 8 o'clock position and into a wisdom tooth connecting mechanism of connector block 22A in the 8 o'clock position. Wire conductor 18A extends proximally in the 2 o'clock position and into a wisdom tooth connecting mechanism of connector block 22A in the 2 o'clock position. Thereby, conductors 18B and 18A are conductively joined at connector block 22A.

Spacer blocks 96 and 98 maintain a general linear shape to the conductors. Spacer blocks 96 and 98 are also comprised of a flexible or compressible material that allows transition assembly 13 to flex during handling of lead 11. These features assist in dissipating stress created in the conductors by preventing the formation of stress points, such as bends or kinks.

Figure 10:
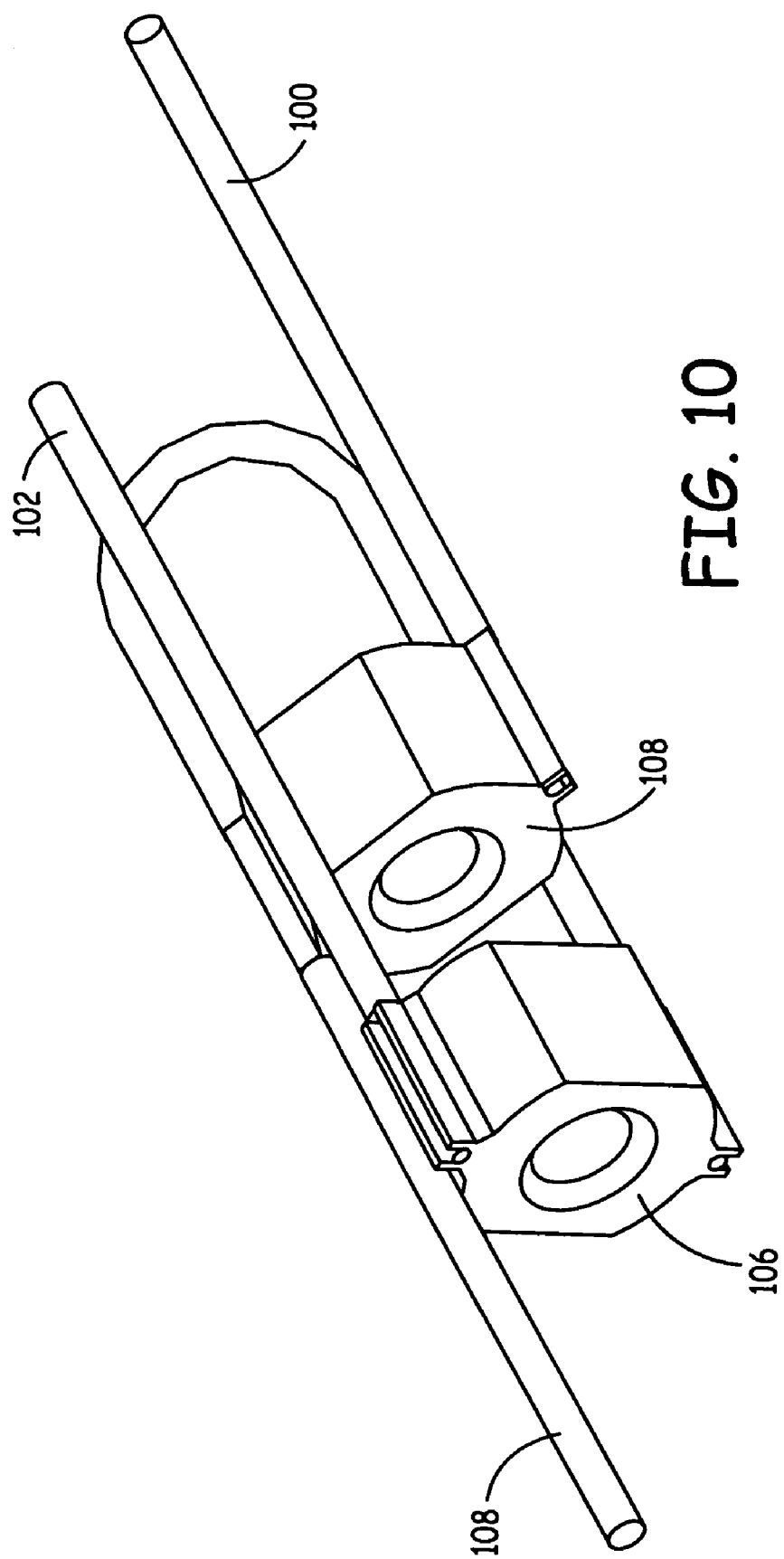
FIG. 10 shows a transition assembly rigged in a bypass configuration.

FIG. 10 shows an alternative embodiment of transition assembly 13 in which the connector blocks are used to create a bypass configuration for conductors 100, 102 and 104. The bypass configuration allows a single conductor lead to be connected with a connector body having two conductors. Conductor 104 extends from a lead at its distal end to transition assembly 13 at its proximal end. Conductor 104 is conductively linked to conductor 102 at connector block 106, and conductively linked to conductor 100 at connector block 108. Conductor 104 extends past connector block 106 and is then joined with a connection mechanism of connector block 108. Conductor 104 curves back around to extend past connector block 108 and into a connecting mechanism of connector block 106. Conductor 102 extends past connector block 108 and into a connecting mechanism of connector block 106, while conductor 100 is joined with a connecting mechanism of connector block 108.

Conductors 102 and 100 are ultimately connected at their proximal ends with circuitry of an IMD, and each is responsible for carrying a distinct signal to or from the circuitry, such as a sense signal and RV defibrillation pulse. Conductor 104 is ultimately connected with one or more electrodes positioned within body tissue at the distal end of conductor 104. The electrode(s) connected to conductor 104 may perform both sensing/pacing and defibrillation functions, depending on whether conductor 100 or 102 is active.

Although the present invention has been described with reference to preferred embodiments, workers skilled in the art will recognize that changes may be made in form and detail without departing from the spirit and scope of the invention.

The invention claimed is:

1. A connector for connecting conductors of a medical electrical lead with an implantable medical device, the connector comprising:
   a connector body having multiple conductors; and
   a modular system of connector blocks for routing and joining the conductors of the medical electrical lead with the multiple conductors of the connector body;
   wherein the connector body having a proximal end for insertion into the implantable medical device and a distal end for connecting with the medical electrical lead, wherein the connector body comprises:
     a central channel running through a longitudinal axis of the connector body; and
     a retainer comprising:
       a cylindrical body having a proximal end for inserting in the central channel.

2. The connector of claim 1 wherein the connector body further comprises:
multiple connector rings positioned near a proximal end of the connector body and conductively linked with the multiple conductors; and
the retainer further comprising:
a center bore extending from a distal end of the cylindrical body and for receiving a coil conductor of the medical electrical lead.

3. The connector of claim 2 wherein the retainer is configured to be press fit with the central channel of the connector body at a proximal end, and with a coil sheathing of the medical electrical lead at a distal end to form an adhesive free connection.

4. The connector of claim 2 wherein a proximal end of the connector body is engagable with a connector pin for an implantable medical device.

5. The connector of claim 4 wherein the connector pin is secured to the proximal end of the connector body with a locking mechanism.

6. The connector of claim 5 wherein the locking mechanism comprises a collar and key that form a yoke to rotatably secure the connector pin within the center channel of the connector body.

7. The connector of claim 1 wherein the connector blocks include blocks having connecting mechanisms for conductively joining the conductors of the lead with conductors of the connector body.

8. The connector of claim 7 wherein the connecting mechanisms include a pair of rails spaced apart to receive a conductor and wherein the pair of rails configured to be crimped around the conductor to form a mechanical connection.

9. The connector of claim 7 wherein the connector blocks having connecting mechanisms include a pair of connecting mechanisms positioned on opposite sides of each connector block.

10. The connector of claim 7 wherein the modular system includes spacer blocks positioned between the connector blocks.

11. The connector of claim 10 wherein each of the spacer blocks comprises a plurality of channels.

12. The connector of claim 10 wherein the spacer blocks are comprised of compressible material.

13. The connector of claim 7 wherein the connector blocks include central bores for positioning the connector blocks around a coil conductor.

14. The connector of claim 13 wherein the connector blocks are rotatable around the coil conductor such that the conductors of the lead can be joined with the multiple conductors without interfering with each other.

15. A connection system for connecting a plurality of electrical conductors of a medical electrical lead to a plurality of conductors of a connector that is insertable into an implantable medical device, the connection system comprising:
a plurality of connector blocks, each block comprising:
a first tooth positioned on the outer diameter of the block for receiving one of the plurality of conductors from the connector; and
a second tooth positioned on the outer diameter of the block approximately one hundred eighty degrees from the first tooth and for receiving one of the plurality of conductors from the lead;
wherein the plurality of connector blocks are axially aligned in a connector housing and circumferentially rotated with respect to one another.

16. The connection system of claim 15 wherein the plurality of connector blocks comprises three connector blocks rotated approximately one hundred twenty degree from each other.

17. The connection system of claim 15 wherein each of the plurality of connector blocks is axially aligned on a coil conductor.

18. The connection system of claim 15 wherein the first and second teeth that are configured to be crimped around the conductors to form a mechanical and electrical connection.

19. The connection system of claim 15 wherein the connector blocks are spaced from one other by spacer blocks.

20. The connection system of claim 19 wherein the spacer block comprises:
a channel passing centrally through the block;
slots positioned apart on an outer periphery of the spacer block.

21. The connection system of claim 19 wherein the spacer blocks comprise compressible material.

22. A medical electrical lead connector comprising:
a connector body having a proximal end for insertion into an implantable medical device and a distal end for connecting with a medical electrical lead, the connector body comprising a generally cylindrical connector body having a central channel running through the axis of the connector body;
a first connector ring positioned near a proximal end of the connector body;
a first conductor wire embedded in the connector body and extending from the distal end to the first connector ring, and conductively linked with the first conductor wire; and
a retainer comprising:
a cylindrical body having a proximal end for inserting in the central channel;
a distal end for receiving a medical electrical lead conductor; and
a center bore extending from the distal end to the proximal end.

23. The medical electrical lead connector of claim 22 wherein the proximal end of the retainer is press fit into the first central channel to form a connection.

24. The medical electrical lead connector of claim 22 wherein the first conductor wire is connected with the first electrode ring by a crimping mechanism.

25. The medical electrical lead connector of claim 22 wherein the distal end of the retainer is connectable with sheathing of a conductor coil.

26. The medical electrical lead connector of claim 25 wherein the distal end of the retainer receives the sheathing to provide an adhesive-free connection.

27. The medical electrical lead connector of claim 22 wherein the proximal end of the connector body is engagable with a connector pin for an implantable medical device.

28. The medical electrical lead connector of claim 27 wherein the connector pin includes a central channel co-axially aligned with the first and second central channels for receiving a stylet.

29. The medical electrical lead connector of claim 27 wherein the connector pin includes a distal end for receiving a proximal end of an coil conductor coil.

30. The medical electrical lead connector of claim 27 wherein the connector pin is secured to the proximal end of the connector body with a locking mechanism.

31. The medical electrical lead connector of claim 22 wherein the connector body includes a second conductor wire embedded in the connector body and conductively connected with a second electrode ring near the proximal end of the connector body.

32. The medical electrical lead connector of claim 31 wherein the connector body includes a third conductor wire embedded in the connector body and conductively connected with a third electrode ring near the proximal end of the connector body.

33. The medical electrical lead connector of claim 32 wherein the first, second and third conductor wires are spaced approximately one hundred and twenty degrees apart around the connector body.

34. The medical electrical lead connector of claim 32 wherein the first, second and third conductor wires are integrally formed with the connector body.

35. The medical electrical lead connector of claim 32 wherein the first, second and third conductor wires include an insulation layer to electrically isolate the conductors from each other.

* * * * *